United States Patent
Boctor et al.

(10) Patent No.: US 12,274,530 B2
(45) Date of Patent: Apr. 15, 2025

(54) NEUROMODULATION BASED NERVE IDENTIFICATION

(71) Applicant: The Johns Hopkins University, Baltimore, MD (US)

(72) Inventors: Emad M. Boctor, Ellicott City, MD (US); Jeeun Kang, Baltimore, MD (US); Arthur L. Burnett, Baltimore, MD (US); Jin U. Kang, Glenelg, MD (US); Maged Harraz, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 319 days.

(21) Appl. No.: 17/277,224

(22) PCT Filed: Sep. 17, 2019

(86) PCT No.: PCT/US2019/051585
§ 371 (c)(1),
(2) Date: Mar. 17, 2021

(87) PCT Pub. No.: WO2020/061097
PCT Pub. Date: Mar. 26, 2020

(65) Prior Publication Data
US 2022/0031166 A1    Feb. 3, 2022

Related U.S. Application Data

(60) Provisional application No. 62/732,808, filed on Sep. 18, 2018.

(51) Int. Cl.
*A61B 5/00* (2006.01)
*A61B 90/00* (2016.01)

(52) U.S. Cl.
CPC ............ *A61B 5/0071* (2013.01); *A61B 5/004* (2013.01); *A61B 5/0095* (2013.01); *A61B 5/407* (2013.01);
(Continued)

(58) Field of Classification Search
CPC .... A61N 7/00; A61N 2007/0021–0026; A61B 5/0071; A61B 5/004; A61B 5/0095;
(Continued)

(56) References Cited

U.S. PATENT DOCUMENTS

2007/0122345 A1 * 5/2007 Golijanin ........... A61K 49/0034
424/9.6
2008/0300655 A1 * 12/2008 Cholette ............ A61N 1/36135
607/60
(Continued)

FOREIGN PATENT DOCUMENTS

WO    WO-2015095344 A1 *    6/2015    ............... A61B 3/10

OTHER PUBLICATIONS

Fried, Nathaniel M., and Arthur L. Burnett. "Novel methods for mapping the cavernous nerves during radical prostatectomy." Nature Reviews Urology 12.8 (2015): 451-460. (Year: 2015).*
(Continued)

*Primary Examiner* — Sean D Mattson
(74) *Attorney, Agent, or Firm* — Harrity & Harrity, LLP

(57) ABSTRACT

A device may obtain imaging data. The imaging data that is obtained depicts one or more body parts of a patient. A voltage sensitive dye may be applied to stain nerve tissue associated with the one or more body parts of the patient. The voltage sensitive dye may be activated by neuromodulation applied to stimulate the nerve tissue. The imaging data may capture a fluorescence of the nerve tissue based on the voltage sensitive dye being activated by neuromodulation. The device may provide the imaging data for display.

20 Claims, 11 Drawing Sheets

(52) U.S. Cl.
CPC .......... *A61B 5/4381* (2013.01); *A61B 5/4893* (2013.01); *A61B 90/37* (2016.02)

(58) Field of Classification Search
CPC ..... A61B 5/407; A61B 5/4381; A61B 5/0036; A61B 5/4893; A61B 90/37; A61B 1/3132; A61B 2034/302
See application file for complete search history.

(56) References Cited

U.S. PATENT DOCUMENTS

| | | | |
|---|---|---|---|
| 2009/0270678 A1* | 10/2009 | Scott | A61B 1/000096 600/109 |
| 2016/0166164 A1* | 6/2016 | Obradovic | A61B 5/7282 600/377 |
| 2016/0242651 A1* | 8/2016 | Wang | A61B 5/6868 |
| 2016/0243234 A1 | 8/2016 | Healey et al. | |
| 2016/0338593 A1 | 11/2016 | Ikehara | |
| 2018/0020921 A1* | 1/2018 | Deisseroth | G01N 21/21 600/407 |
| 2019/0254545 A1* | 8/2019 | Jeong | A61B 5/24 |
| 2021/0236657 A1* | 8/2021 | Gibbs | A61K 9/1075 |

OTHER PUBLICATIONS

International Search Report and Written Opinion for Application No. PCT/US2019/051585, mailed on Jan. 3, 2020, 10 pages.

\* cited by examiner

NEUROMODULATION BASED NERVE IDENTIFICATION

RELATED APPLICATIONS

This application is a 371 national stage of PCT Application PCT/US2019/051585 filed on Sep. 17, 2019, which claims priority to U.S. Provisional Patent Application No. 62/732,808, filed on Sep. 18, 2018, both of which are hereby expressly incorporated by reference herein.

GOVERNMENT LICENSE RIGHTS

This invention was made with U.S. Government support under grant R24MH106083-03, awarded by the Department of Health and Human Services, the National Institutes of Health (NIH). The U.S. Government has certain rights in the invention.

BACKGROUND

A prostatectomy, such as a laparoscopic radical prostatectomy, a radical retropubic prostatectomy, and/or the like, may be performed for a patient with prostate cancer to remove a prostate of the patient. Laparoscopic prostatectomy may be associated with reduced scarring, bleeding, catheterization time, hospital stay duration, and/or the like relative to radical retropubic prostatectomy and may be performed with a similar level of efficacy. Robot-assisted radical prostatectomy has been introduced to achieve a similar level of efficacy with improved preservation of erectile nerves as a result of improved endoscopic vision relative to previous techniques for prostatectomy.

During prostate cancer surgeries, such as prostatectomies, a surgeon may attempt to preserve nerve tissue to minimize a negative patient impact as a result of a surgery. Cavernous nerves, such as the erectile nerves, may be disposed approximately 2.8 millimeters (mm) from a prostate of a patient. Moreover, each individual cavernous nerve may be associated with a size of between approximately 10 microns and 100 microns. A position of the individual cavernous nerves may be different for each patient.

SUMMARY

According to some implementations, a method may include activating a voltage sensitive dye using neuromodulation. The activation may be performed based on the voltage sensitive dye binding to a cell membrane associated with tissue of a patient. The method may include obtaining imaging data regarding the tissue based on activating the voltage sensitive dye using neuromodulation. The method may include causing the imaging data to be displayed.

According to some implementations, a device may include one or more memories; and one or more processors, communicatively coupled to the one or more memories, to obtain imaging data. The imaging data that is obtained may depict one or more body parts of a patient. A voltage sensitive dye may be applied to bind to nerve tissue associated with the one or more body parts of the patient. The voltage sensitive dye may be activated by ultrasound neuromodulation applied to stimulate the nerve tissue. The imaging data may capture a fluorescence of the nerve tissue based on the voltage sensitive dye being activated by ultrasound neuromodulation. The one or more processors may provide the imaging data for display.

According to some implementations, a method may include communicating, with a surgical system, to cause the surgical system to perform one or more incisions into a patient. The method may include communicating with the surgical system, to cause the surgical system to activate, using ultrasound neuromodulation, at least a portion of a voltage sensitive dye. The voltage sensitive dye may have been applied to nerve tissue associated with a prostate. Activating a portion of the voltage sensitive dye may cause a fluorescence associated with at least a portion of the nerve tissue. The method may include communicating, with the surgical system, to cause the surgical system to obtain imaging data of the fluorescence associated with at least the portion of the nerve tissue. The imaging data may identify a nerve map of at least one of: one or more nerve bundles associated with the prostate, or one or more nerve branches associated with the prostate. The method may include providing, by the device, the imaging data for display, to allow a prostatectomy to be performed in a manner that uses the nerve map to avoid disturbance of the nerve tissue.

DETAILED DESCRIPTION

Figure 1A:
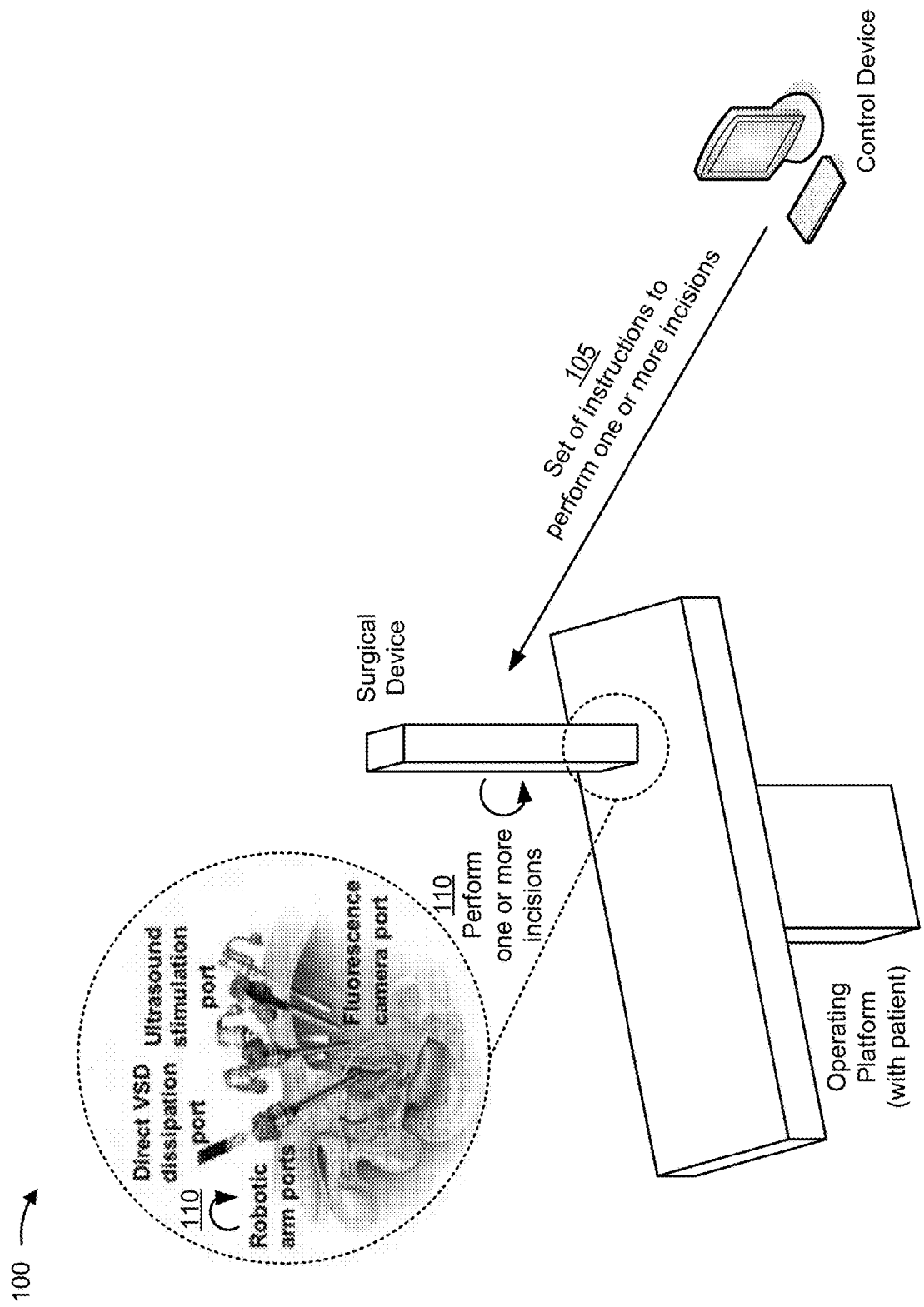
FIGS. 1A-1F are diagrams of one or more example implementations described herein.

The following detailed description of example implementations refers to the accompanying drawings. The same reference numbers in different drawings may identify the same or similar elements.

There are several nerve stimulation methods to selectively stimulation the erectogenic nerve network in a patient. For example, electrical nerve stimulation, optical nerve stimulation, and/or the like may be used to image nerve tissue. On the other hand, imaging and spectroscopy techniques may be used to image nerve tissue. The imaging and spectroscopy techniques may include a technique using fluorescence, multiphoton microscopy, coherent anti-Stokes Raman spectroscopy, optical coherent tomography, ultrasonography, magnetic resonance imaging (MRI), and/or the like.

However, each technique may be associated with one or more limitations that reduce a usefulness in preventing damage to nerve tissue (e.g., damage that may occur during a surgery, such as a prostatectomy). For example, electrical stimulation may be inconsistent with low specificity and high false positive responses; optical nerve stimulation may be associated with a relative slow nerve response; ultrasound and magnetic resonance imaging based techniques may be associated with relatively poor spatial resolution (e.g., which may be inappropriate to delineate details in an erectogenic nerve network); optical microscopy and optical coherent tomography may be associated with a relatively shallow imaging depth; fluorescence and magnetic resonance imaging may be associated with relatively slow acquisition time; and dye-based fluorescence may be associated with safety concerns for the patient.

Additionally, many techniques are able to only indirectly identify nerve tissue. For example, fluorescence and magnetic resonance imaging may identify fatty tissues, such as lipids, and may determine that nerve tissue is present based on detection of fatty tissues that are often found near nerve tissue. However, indirect and/or inaccurate identification of nerve tissue may cause a surgeon to accidentally damage or sever one or more nerves during a surgery, such as a prostatectomy. A damaged or severed nerve may lose nerve function (e.g., a damaged erectile nerve may cause a patient to experience erectile dysfunction).

Furthermore, there is no technique available for identification of a function of specific nerves that are part of one or more nerve branches and/or nerve bundles. For example, in an erectogenic nerve branch, a first nerve may perform a first function, a second nerve may perform a second function, and/or the like. Additionally, a nerve may have a function that is more important than one or more other nearby nerves. However, without a way to identify the function of the nerves, a surgeon may not know which nerves must be avoided during surgery (e.g., to avoid risking damaging or severing a nerve with an important function).

Some implementations, described herein, provide tissue imaging for surgical procedures, diagnostic procedures, and/or the like. For example, some implementations, described herein, may use voltage-sensitive dye, ultrasound neuromodulation, photoacoustic and/or fluorescence imaging, and/or the like to provide real-time or near-real time imaging of nerve tissue with a threshold level of imaging depth. In this way, a nerve-sparing prostatectomy (e.g., a robot assisted radical prostatectomy) may be performed with reduced likelihood of nerve tissue damage. Moreover, some implementations, described herein, may be used to perform imaging of another type of tissue based on excitation of a voltage membrane and imaging of a variation in the voltage membrane. For example, a surgical device may perform imaging of nerve tissue, cancer tissue, and/or the like, such as for surgical procedures, diagnostic procedures, and/or the like.

In this way, some implementations described herein may improve surgical imaging by improving imaging resolution, imaging accuracy, imaging depth, and/or the like. For example, some implementations, described herein, may improve surgical imaging by providing real-time or near real-time imaging of nerve tissue based on activating a voltage sensitive dye (VSD) and utilizing ultrasound neuromodulation. Moreover, based on activating the VSD and utilizing ultrasound neuromodulation, risk of surgical complications will be reduced, time to perform surgeries may be reduced, the surgeries may be performed in a less invasive manner, and/or the like relative to other imaging techniques.

FIGS. 1A-1F are diagrams of one or more example implementations 100 described herein. Example implementation(s) 100 include a control device and a surgical device. As shown in FIGS. 1A-1F, the control device may communicate with the surgical device to allow the surgical device to use voltage sensitive dye (VSD), ultrasound neuromodulation, fluorescent and/or photoacoustic imaging, and/or the like, to identify nerve tissue in a vicinity of a prostate of a patient. This may allow the surgical device (and/or a surgeon) to perform a prostatectomy, such as a robot assisted radical prostatectomy, to remove the prostate in a manner that avoids disturbance of the nerve tissue.

Although some implementations, described herein, describe the prostatectomy as being a robot assisted radical prostatectomy, some implementations described herein may be used to perform imaging for another procedure, such as a laparoscopic prostatectomy, a surgical procedure involving organs other than the prostate, a nerve-sparing surgical procedure, a diagnostic procedure, a non-surgical procedure (e.g., a therapeutic procedure), and/or the like. Additionally, one or more implementations described herein may refer to delivery of voltage sensitive dye. The voltage sensitive dye may be delivered topically, via systemic injection, and/or the like.

The control device may, for example, be a desktop computer, a laptop computer, a mobile device, and/or the like, and may be configured to communicate with the surgical device via one or more communication interfaces. In some implementations, the control device may be a computer located in a room being used for the prostatectomy. The one or more communication interfaces may include an application programming interface (API), a radio interface, and/or another type of interface.

The surgical device may, for example, include a surgical robot with a set of devices for performing a surgical incision, VSD staining, ultrasound excitation, image capturing and reporting, a surgical procedure, and/or the like. In this case, the set of devices may include one or more surgical robotic operating arms (that include one or more robotic arm ports), a VSD dissipation device (e.g., that includes a direct VSD dissipation port), an ultrasound stimulation device (e.g., with an ultrasound stimulation port), one or more camera devices (e.g., a white light image capturing device, a fluorescent image capturing device, a laser device, and/or the like), one or more transfuser devices (e.g., capable of capturing and/or converting sound waves), a voltage membrane variation measurement device, and/or the like.

As shown in FIG. 1A, and by reference number 105, the control device may provide, to the surgical device, a set of instructions to perform one or more incisions. For example, the control device may provide a set of instructions to the surgical device to perform one or more abdominal incisions for imaging associated with the prostatectomy. The set of instructions may include an instruction that indicates to perform an incision, an instruction that indicates a position at which to place a component of the surgical device (e.g., a target area of the patient's abdomen), and/or the like.

In some implementations, the control device may provide the surgical device with instructions to perform incisions relating to another type of surgical procedure. For example, the control device may provide the surgical device with instructions to perform one or more incisions relating to a cancer detection procedure, a cancer removal procedure, and/or another type of procedure for which tissue imaging is to be performed (e.g., nerve tissue imaging, cancer tissue imaging, and/or the like).

As shown by reference number 110, the surgical device may perform the one or more incisions. For example, the surgical device may, based on receiving the set of instructions, perform one or more abdominal incisions for imaging that will be used for the prostatectomy. In some implementations, the one or more incisions may be performed entirely by the surgical device. In some implementations, a surgeon may perform the one or more incisions with the surgical device. In some implementations, a surgeon may perform one or more incisions separate from the surgical device.

In this way, the control device causes the surgical device to perform the one or more incisions.

Figure 1B:
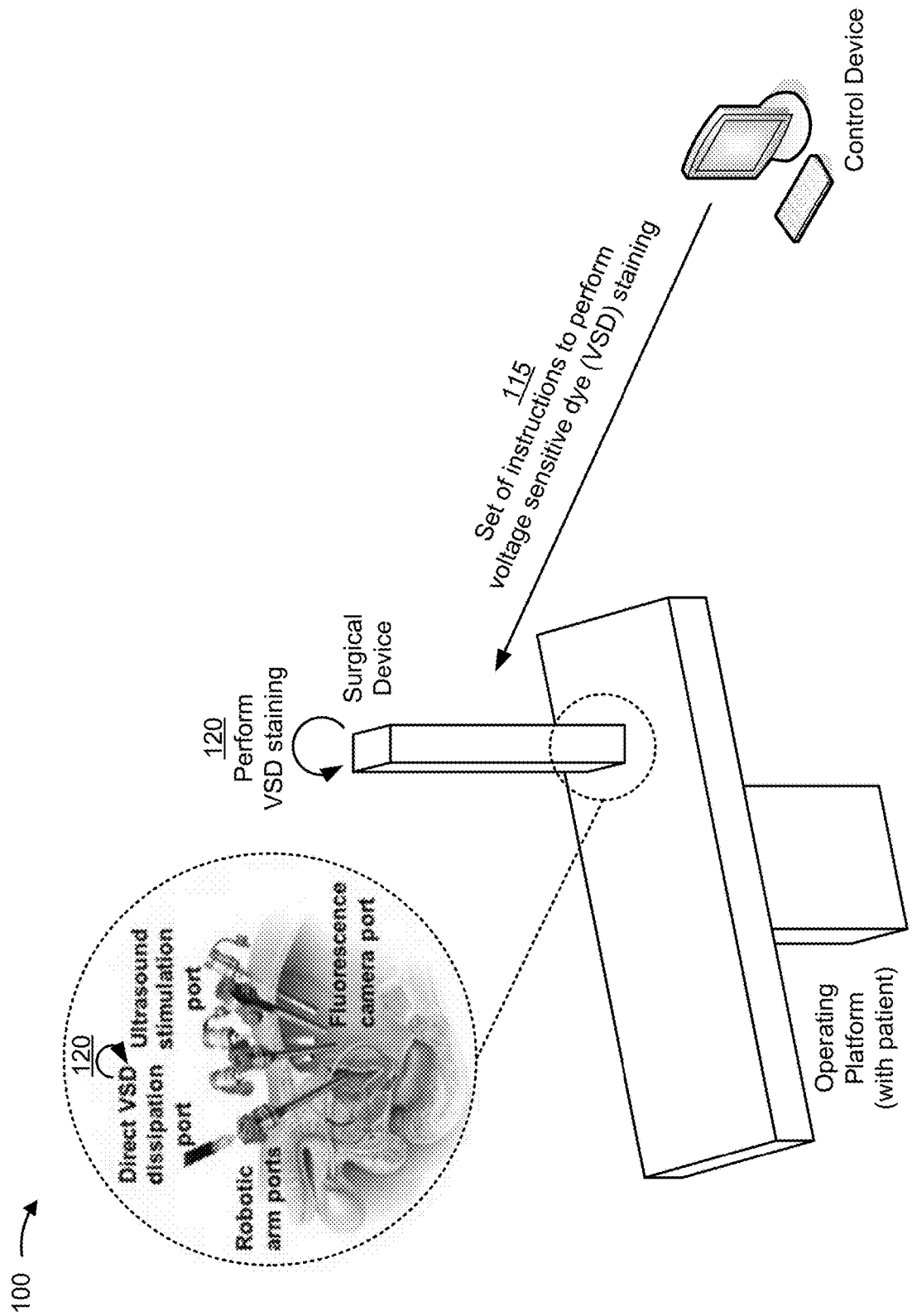

As shown in FIG. 1B, and by reference number 115, the control device may provide, to the surgical device, a set of instructions to perform VSD staining. For example, the control device may provide the VSD dissipation device of the surgical device with a set of instructions to perform VSD staining. The control device may provide the set of instructions to perform VSD staining based on receiving an indication that the one or more incisions have been completed, based on receiving a request from the surgeon, and/or based on another type of trigger. The set of instructions may indicate to perform VSD staining, may identify a location at which to apply the VSD (e.g., a location of a surface of the prostate of the patient, such as a nerve surface in a prostatic fascia), may identify which VSD to apply (e.g., if the surgical device is capable of applying different types of VSD), may indicate a recommended staining concentration of the VSD, may indicate a duration at which to apply the VSD, may indicate a recommended depth at which the nerve tissue is to be stained, and/or the like. In some implementations, the voltage sensitive dye may be bound to a cell membrane associated with tissue of a patient based on delivery of the voltage sensitive dye via a surgical incision, based on delivery of the voltage sensitive dye via a topical approach, and/or the like.

In some implementations, the control device may select a particular VSD that optimizes identification of one or more nerve bundles and/or nerve branches. For example, a group of VSD may have different response times, intensity levels, absorption and/or emission levels, reversibility characteristics, and/or the like. In this case, the control device may be configured with a set of VSD selection rules and/or threshold values that may be applied to select the particular VSD. In this way, the control device may select the VSD that has a lowest response time, that has a threshold intensity level, that has an absorption level sufficient to stain the nerve tissue at the recommended depth, and/or the like.

In some implementations, the control device may have been configured with the set of rules and/or threshold values based on research performed by a team of scientists. To provide an example, the team of scientists may have determined that optimal VSD have absorbance and fluorescence emission peaks at near infrared regions (e.g., 800 nanometers (nm) and 830 nm, respectively). This may allow the control device to be configured with rules and/or threshold values that ensure that optimal VSD are selected for VSD staining.

In some implementations, the control device may use machine learning to select a particular VSD. For example, the control device may have access to a data model that has been trained using machine learning to score a set of available VSDs and to identify a VSD based on likelihoods of each respective available VSD being an optimal VSD for identifying the nerve tissue associated with the prostate.

As shown by reference number 120, the surgical device may perform VSD staining. For example, the surgical device (e.g., using a spraying tool of the VSD dissipation device) may perform VSD staining by applying the VSD to stain the surface of the prostate and/or an area in a vicinity of the prostate.

In some implementations, the surgical device may perform a spraying procedure to cause the nerve tissue associated with a periprostatic fascia of the prostate to be stained with the VSD, thereby enabling identification of the nerve tissue that is disposed onto and/or located in the vicinity of the prostate of the patient. In some implementations, the spraying procedure may utilize a direct VSD dissipation approach (and/or a similar type of approach), which may allow an unstacked area near the nerve tissue and/or an unstained area of the nerve tissue to lower the nerve tissue contrast (and make identification of the nerve tissue easier when presented for display).

In some implementations, the surgical device may cause the VSD staining to occur in connection with a particular timing procedure. For example, the set of instructions to perform VSD staining may have specified to perform VSD staining for a threshold time period (e.g., eight minutes, ten minutes, twelve minutes, and/or the like) via the spraying procedure. In this case, VSD staining may occur between creation of surgical incisions and removal of the prostatic fascia, thereby enabling imaging to occur without a delay to the surgical procedure. Consequently, the VSD may be applied with reduced risk to the patient relative to systemic injection. In another example, the VSD may be applied using systemic injection. In some implementations, the surgeon may perform VSD staining separate from the surgical device.

In this way, the control device causes the surgical device to perform VSD staining.

Figure 1C:
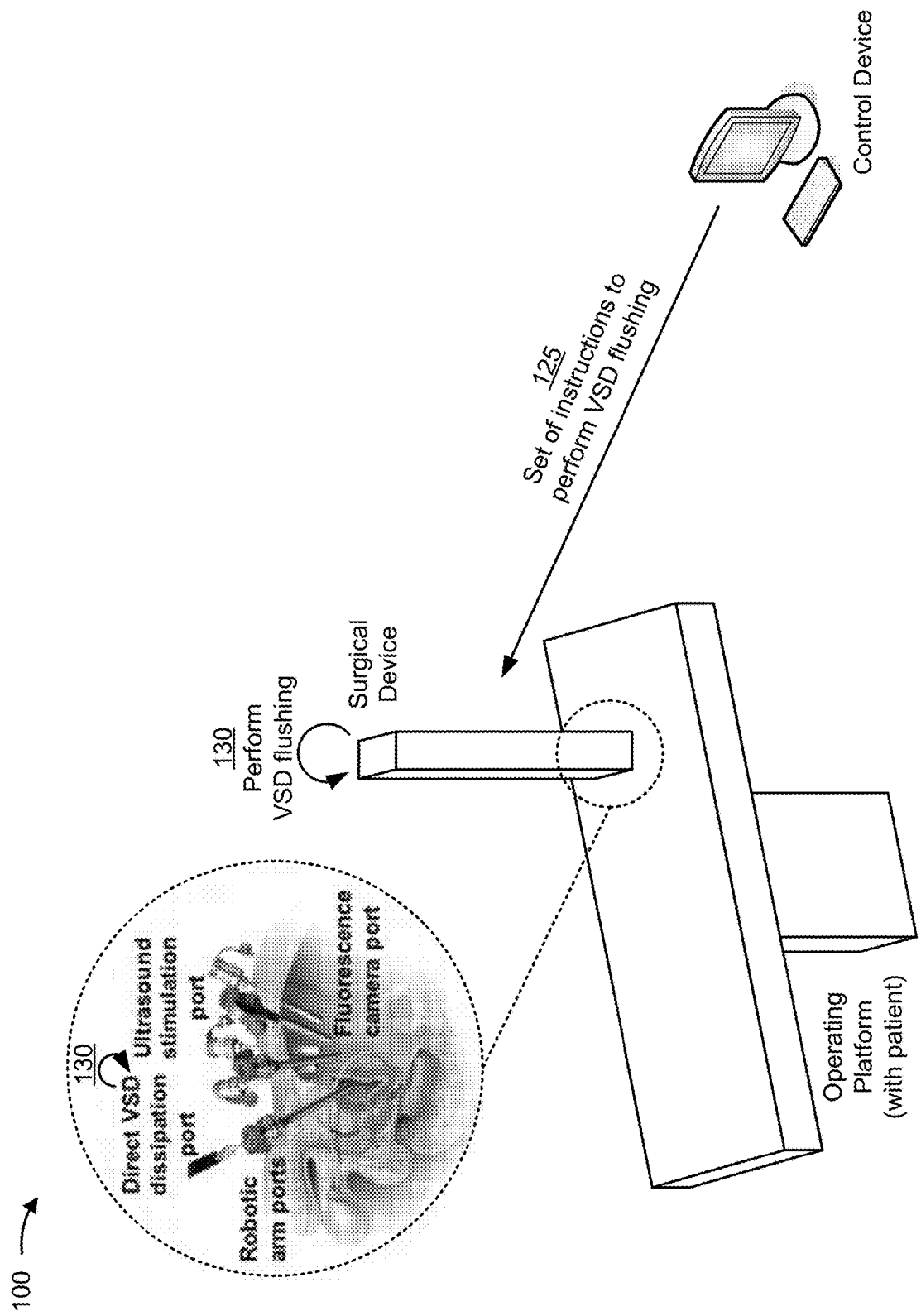

As shown in FIG. 1C, and by reference number 125, the control device may provide, to the surgical device, a set of instructions to perform VSD flushing. For example, the control device may provide the surgical device with a set of instructions to perform VSD flushing based on receiving an indication that VSD staining has been completed, based on receiving an indication that the VSD has binded to a cell membrane associated with the nerve tissue of the patient, based on receiving a request from the surgeon, and/or based on another type of trigger. The set of instructions to perform VSD flushing may indicate a manner in which to perform the VSD flushing, a duration at which to perform the VSD flushing, and/or the like.

As shown by reference number 130, the surgical device may perform VSD flushing. For example, the surgical device (e.g., using a flushing tool of the VSD dissipation device) may flush at least a portion of the VSD based on receiving the set of instructions to perform VSD flushing, based on a timing configuration being satisfied (e.g., based on expiration of a threshold time period, and/or the like), and/or the like. To flush at least a portion of the VSD, the surgical device may apply water or a similar cleansing agent to the nerve tissue and/or to the surface of the prostate that has been stained and/or that is bound to the VSD.

In some implementations, the surgical device may flush a first portion of the VSD but not a second portion of the VSD. For example, the surgical device may flush a first portion of the VSD that is not bound at a cell membrane level (e.g., from the prostate surface). In this case, surgical device may not flush a second portion of the VSD that is bound at the cell membrane level (e.g., to nerve tissue disposed on and/or in a vicinity of the prostate). Consequently, the second portion of the VSD will remain for excitation using ultrasound neuromodulation, as will be described further herein.

In this way, the control device causes the surgical device to perform VSD flushing.

Figure 1D:
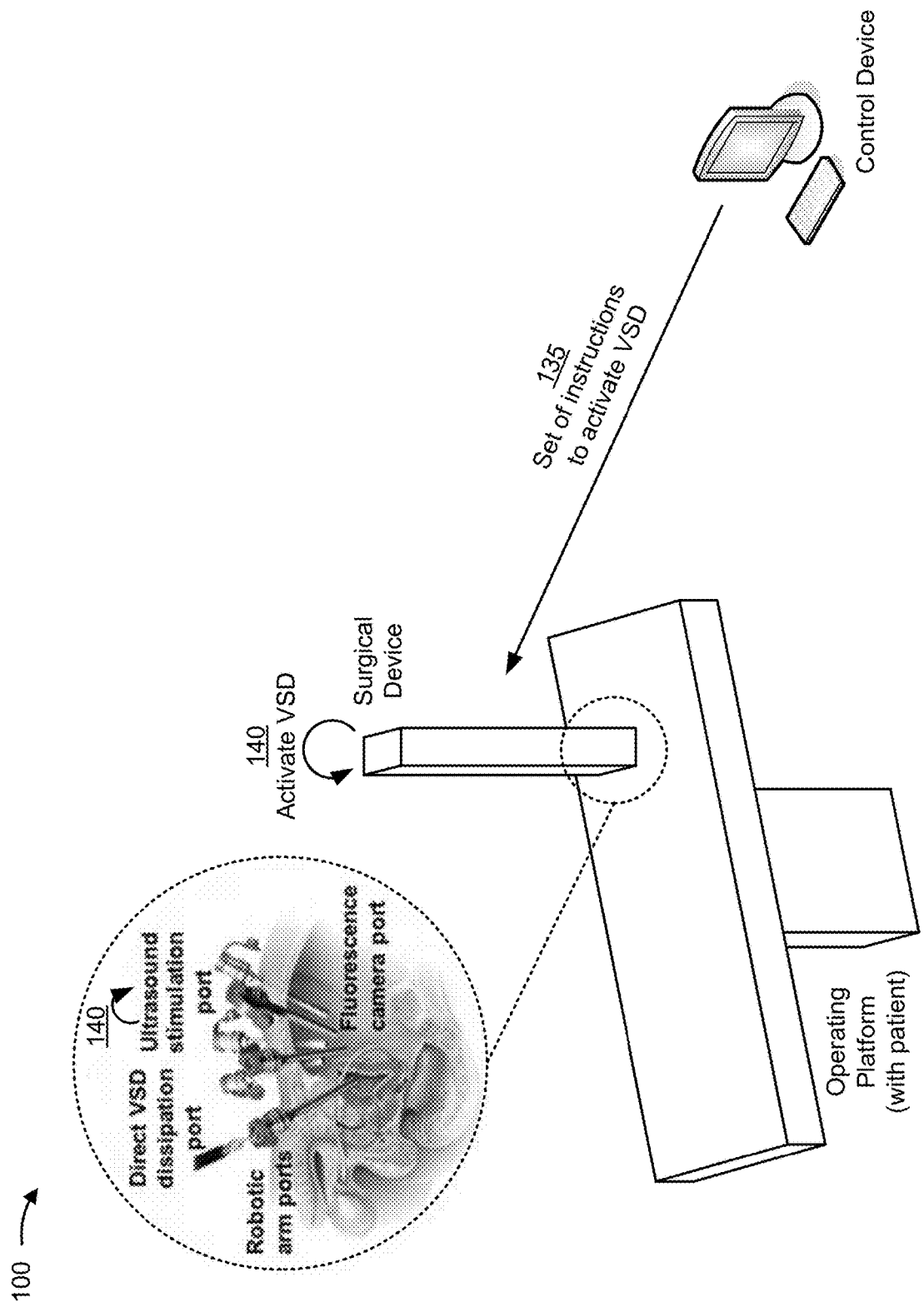

As shown in FIG. 1D, and by reference number 135, the control device may provide, to the surgical device, a set of instructions to activate the VSD. For example, the control device may provide, to the ultrasound stimulation device of the surgical device, the set of instructions to activate the VSD. As used herein, activating the VSD may involve activating a VSD stain, such as a VSD stain that has not been flushed, activating the VSD that is bound to the cell membrane associated with the nerve tissue of the patient, and/or the like. The set of instructions to activate the VSD may be provided based on receiving an indication that VSD flushing has been completed, based on receiving a request from the surgeon, and/or based on another type of trigger.

In some implementations, the set of instructions may identify an activation technique to use to activate the VSD (e.g., a technique using ultrasound neuromodulation), a type of stimulation to use for the activation technique (e.g., a non-invasive stimulation via a spinal cord of the patient, a laparoscopic stimulation on a surgical site associated with the one or more incisions that were made, a transrectal stimulation via a rectum of the patient, and/or the like), and/or the like. Additionally, or alternatively, the set of instructions may identify an excitation time (e.g., a duration for which to excite neurons of the VSD), an excitation energy level (e.g., a power level), an excitation frequency (e.g., a wavelength of energy), an excitation pattern (e.g., a pattern of pulsing of ultrasound energy), an excitation delivery method (e.g., non-invasive via a sacral plexus of the patient, such as via sacral 2 to sacral 4), and/or the like.

In some implementations, the control device may select a particular type of stimulation to use when activating the VSD. For example, an optimal type of stimulation may vary depending on an anatomical distribution of nerves associated with the spine and/or the prostate of the patent. Specifically, the optimal type of stimulation may vary depending on the distribution of nerves from sacral segments of the spine through the prostate (e.g., a second sacral segment, a third sacral segment, a fourth sacral segment, and/or the like). Consequently, the control device may be configured to select a particular type of simulation (e.g., the non-invasive stimulation, the laparoscopic stimulation, the transrectal simulation, and/or the like) based on the distribution of nerves from the sacral segments of the spine through the prostate. In this way, the control device selects a type of stimulation that will lead to optimal nerve bundle identification (and/or optimal nerve branch identification), as described further herein.

Additionally, or alternatively, the control device may select a particular excitation configuration that is to be used to activate the VSD. For example, the control device may be configured with a set of excitation configurations and may select a particular excitation configuration that corresponds to a particular excitation time, a particular excitation energy level, a particular excitation frequency, a particular excitation pattern, a particular excitation delivery method, and/or the like. In this case, the control device may provide a set of instructions that corresponds to the selected excitation configuration to the surgical device.

In some implementations, the control device may select a type of stimulation and/or an excitation configuration using a data model that has been trained using machine learning. For example, the control device may have access to a data model that has been trained on historical data, such that the data model is able to score types of stimulation based on a likelihood of particular types of stimulation being optimal given an anatomical distribution of nerves (e.g., an image of the anatomical distribution may be provided as input to the data model). Additionally, or alternatively, the control device may have access to a data model that has been trained on historical data, such that the data model is able to score types of excitation configurations based on a likelihood of particular excitation configurations being optimal given a particular input dataset (e.g., which may identify an excitation time, an excitation energy level, an excitation frequency, an excitation pattern, and/or the like).

As shown by reference number 140, the surgical device may activate the VSD. For example, the surgical device (e.g., using the ultrasound stimulation device) may activate the VSD based on receiving the set of instructions to activate the VSD and/or based on another type of trigger. The ultrasound stimulation device may include one or more probes that are capable of transmitting ultrasound energy in a manner described below.

In some implementations, the surgical device may activate the VSD using ultrasound neuromodulation. For example, the ultrasound stimulation device may perform ultrasound neuromodulation by transmitting ultrasound energy toward neurons in a spinal cord of the patient to excite neurons associated with a prostatic plexus (e.g., at thoracic 11 to lumbar 2, sacral 2 to sacral 4, and/or the like), neurons associated with the surface of the prostate, neurons associated with the nerve tissue, and/or the like. This may activate the VSD (e.g., the portion of the VSD the remains stained) in a manner that causes a fluorescence, in a manner that causes a photoacoustic effect, and/or the like. By using ultrasound neuromodulation to excite the nerve tissue, imaging of nerve tissue is enabled without invasive excitation (e.g., without requiring invasive surgery at the excitation point, such as at the spinal cord), thereby improving imaging relative to invasive excitation procedures, such as electrical stimulation, and/or the like. Additionally, by activating the VSD in a manner that causes a fluorescence and/or a photoacoustic effect, a voltage membrane variation of the VSD may be identifiable via one or more imaging techniques, as will be described further herein.

Additionally, or alternatively, the surgical device may apply the ultrasound energy using one or more other types of stimulation. For example, the ultrasound stimulation may be applied using a laparoscopic stimulation (e.g., using a drop-in probe disposed in a surgical incision), a transrectal stimulation (e.g., a transrectal ultrasound in a rectum of the patient), and/or the like.

In some implementations, the surgical device may selectively activate a portion of the VSD (e.g., a subset of the remaining VSD stain). For example, the surgical device may, using ultrasound neuromodulation, identify a portion of the VSD that is bound to the nerve tissue (e.g., bound at a cell membrane level to the nerve tissue), and may selectively activate the identified portion of the VSD. In some implementations, the selection may be performed by the control device.

In some implementations, the surgical device may activate at least a portion of the VSD using another type of neuromodulation (e.g., other than ultrasound). For example, the surgical device may activate at least a portion of the VSD using thermal energy, electrical current excitations, and/or any other technique capable of stimulating erectile function.

In this way, the control device causes the surgical device to activate the VSD.

Figure 1E:
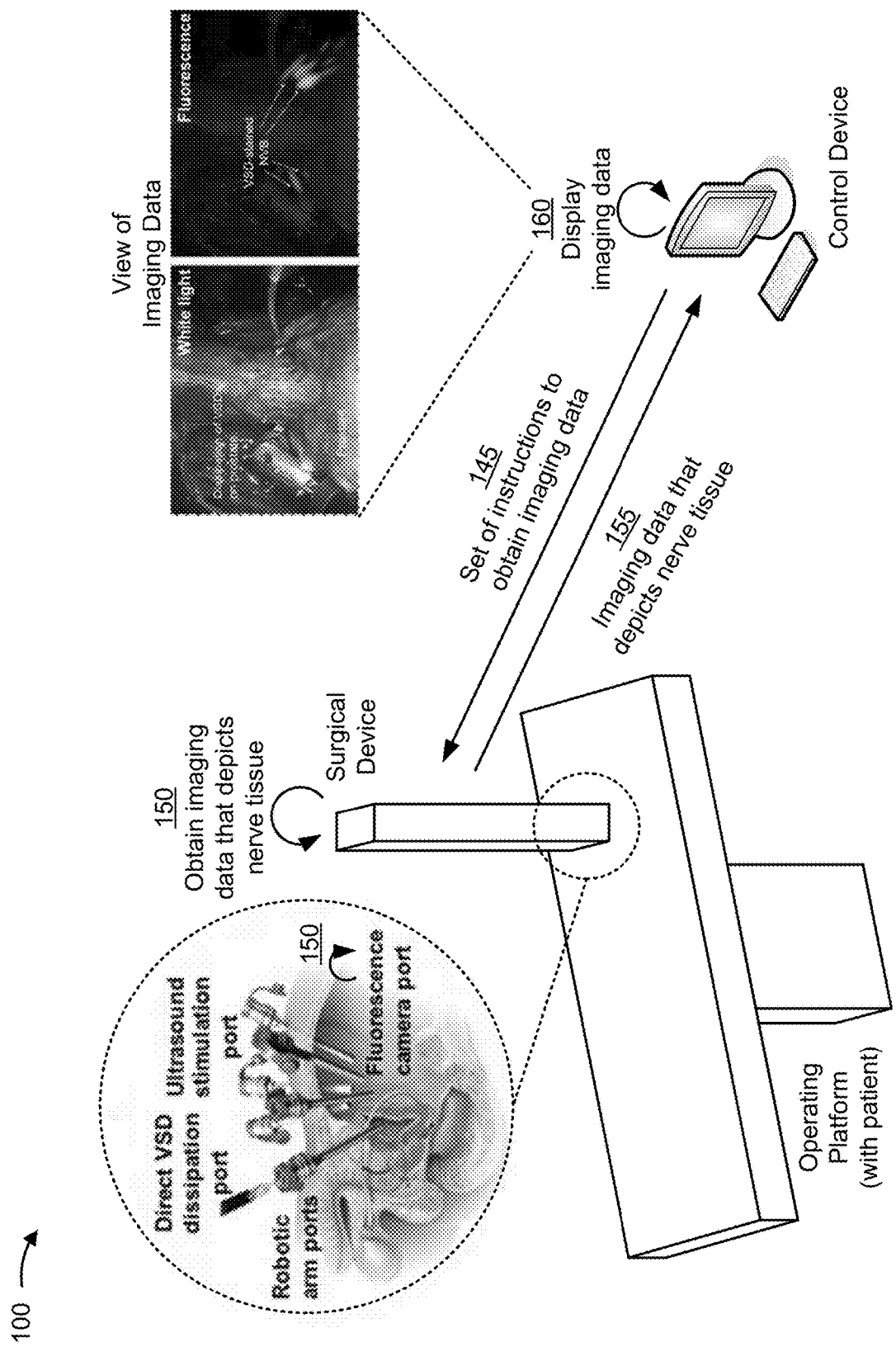

As shown in FIG. 1E, and by reference number 145, the control device may provide, to the surgical device, a set of instructions to obtain imaging data. For example, the control device may provide the surgical device with a set of instructions to obtain imaging data based on receiving an indication that the VSD has been activated (e.g., using ultrasound neuromodulation) and/or based on another type of trigger. The set of instructions may identify one or more camera devices that are to be used to obtain the imaging data, may identify one or more image configuration settings for a given camera device, and/or the like. The one or more image configuration settings may include a configuration indicating a depth that specifies how much of a nerve bundle and/or a nerve branch is to be captured in an image, a configuration indicating a number of images to capture, a configuration indicating a pixilation or minimum quality that must be used when capturing images, and/or the like).

To provide a specific example, the control device may provide instructions indicating to position a laser within several millimeters of a point of incision (e.g., using a fixed angle and distance from the surgical device), instructions to use a fluorescent camera and/or a photoacoustic probe to capture imaging data at the illumination point identified by the laser, an instruction to track the incision point over time, and/or the like. In some implementations, the control device may use machine learning to identify optimal camera configurations to recommend to the surgical device.

As shown by reference number 150, the surgical device may obtain imaging data that depicts nerve tissue. For example, the surgical device may obtain imaging data that depicts nerve tissue that is disposed on and/or located in the vicinity of the prostate. The imaging data may be obtained based on receiving the set of instructions to obtain the imaging data, based on activating the VSD stain using ultrasound neuromodulation, and/or based on another type of trigger. The imaging data may be obtained using the one or more camera devices (e.g., the white light image capturing device, the fluorescent image capturing device, the laser device, and/or the like), the one or more transfuser devices, and/or the like.

In some implementations, the surgical device may use the fluorescence camera device to obtain imaging data of fluorescent images that depict the fluorescence associated with the nerve tissue. For example, the fluorescence camera device may capture imaging data of fluorescent images that depict the fluorescence associated with the nerve tissue and may provide the imaging data to one or more processors of the surgical device. In some cases, the fluorescence depicted by the fluorescent images may be used to identify a nerve map of one or more nerve bundles associated with the nerve tissue, one or more nerve branches associated with the nerve tissue, and/or the like. The nerve map may identify specific nerve bundles and/or specific nerve branches of a particular nerve bundle. In this way, the fluorescent images that depict the fluorescence may be used to identify the nerve tissue that has been stained by the VSD, to identify specific nerve bundles and/or nerve branches, to identify specific nerves within the nerve bundles and/or nerve branches, and/or the like.

Additionally, or alternatively, the surgical device may use the white light image capturing device to obtain imaging data of white light images of the nerve tissue. The white light images may be displayed in contrast with the fluorescent images, as described further herein.

Additionally, or alternatively, the surgical device may use the laser device (e.g., capable of emitting pulse laser light) to obtain imaging data of photoacoustic images that are based on the photoacoustic effect caused by the VSD being activated by ultrasound neuromodulation. For example, the laser device may emit a pulse laser light at the nerve tissue identified by fluorescence. This may cause biological tissue to absorb the pulse laser light, causing thermal elastic expansion. Thermal elastic expansion may cause sound waves to be emitted, which may be captured by one or more transducers (e.g., an ultrahigh frequency transducer) of the surgical device. The one or more transducers may convert the sound waves to electrical signals, such that one or more processors of the surgical device may convert the electrical signals to the imaging data of the photoacoustic images.

In some implementations, the surgical device may obtain imaging data that captures a threshold level of depth of one or more nerve bundles and/or their branches. For example, the surgical device may obtain imaging data that depicts one or more nerve bundles at a depth of at least two or three millimeters. In this way, the surgical device obtains imaging data that is superior to other imaging data obtained by inferior pure optical imaging techniques that are able to capture images of the nerve tissue at only low depths (e.g., a depth of less than two or three millimeters).

In some implementations, the surgical device may periodically obtain imaging data. For example, the set of instructions to obtain the imaging data may specify to periodically obtain imaging data throughout a surgical procedure. In some cases, the surgical device may obtain imaging data after each time that the VSD is activated during the surgical procedure. In this way, the surgical device improves an accuracy of imaging and reduces a likelihood of surgical complication relative to providing static imaging. Moreover, in this way, the surgical device may provide real-time or near-real time imaging of nerve tissue to facilitate surgical procedures.

As shown by reference number 155, the surgical device may provide the imaging data that depicts the nerve tissue to the control device. For example, the surgical device may provide the imaging data to the control device based on obtaining the imaging data and/or based on another type of trigger.

As shown by reference number 160, the control device may provide the imaging data for display. For example, the control device may provide the imaging data for display via a user interface to allow the surgeon to visualize the nerve tissue.

In some implementations, the control device may provide the imaging data for display in a manner that contrasts stained nerve tissue with tissues and/or body parts that are not stained. For example, the control device may provide, for display, a visible (e.g., white) light image of the prostate and a fluorescent image of the prostate (e.g., showing fluorescence contrast of nerve tissue based on VSD activation). In some implementations, the control device may provide the visible light image and/or a fluorescence image of the activated VSD via multiple user interface views, via a single user interface view (e.g., a side-by-side view, an overlaid view, an augmented reality visualization, etc.), and/or the like.

In some implementations, the control device may provide, for display, the imaging data that identifies the nerve map of the nerve tissue. For example, the control device may provide the imaging data that identifies the nerve map for display in a manner that allows the surgeon to view specific nerves included in the one or more nerve bundles that are part of the nerve tissue. Additionally, or alternatively, the control device may display the nerve map in a manner that assigns different colors to different nerves, based on a confidence level in an identified location of a given nerve, based on a level of importance of a function of a given nerve, and/or the like. In this way, the control device provides the nerve map for display in a manner that allows the prostatectomy to be performed without damaging the nerve tissue.

In some implementations, the control device may label imaging data and may provide labeled imaging data for display. For example, the control device may process the imaging data to identify a position of one or more nerve bundles (e.g., within an image), to identify a position of one or more nerve branches, to identify a position of one or more nerves associated with nerve bundles, to identify a function of one or more nerves, to identify a state of one or more nerves (e.g., healthy, unhealth, and/or the like), and/or the like. In some implementations, the control device may label the imaging data by identifying a position of a nerve, a nerve branch, and/or a nerve bundle. In this case, the control device may identify the position of the nerve, the nerve branch, and/or the nerve bundle based on the fluorescence caused by the VSD being activated by ultrasound neuromodulation, based on the photoacoustic effect caused by the laser being emitted at an area identified by the activated VSD, based on a combination of the fluorescence and/or the photoacoustic effect, based on a measurable difference between the fluorescence and the photoacoustic effect, and/or the like. The labeled imaging data may be provided for display as part of the nerve map.

Additionally, or alternatively, the control device may periodically receive imaging data and may label the imaging data by comparing imaging data at various time periods. For example, the control device may obtain first imaging data before activation of the VSD, second imaging data during activation of the VSD, third imaging data after activation of the VSD, and/or the like. In this case, the control device may identify, within particular images, the position of the nerve tissue, the position of the one or more nerve bundles, the position of the one or more nerve branches, the position of the one or more nerves associated with the one or more nerve bundles, and/or the like, based on a variation in fluorescence caused by ultrasound neuromodulation. The control device may identify the positions using one or more computer vision techniques and/or similar types of techniques.

In this way, the control devices provides labeled imaging data for display to allow the surgeon to visualize a position of nerves that are part of the nerve tissue (e.g., relative to the prostate, relative to one or more components and/or tools of the surgical device, relative to fatty tissues near the nerves, and/or the like).

In some implementations, the control device may use one or more machine learning techniques to label imaging data and to provide the labeled imaging data for display. For example, the control device may use one or more machine learning techniques, such as a pattern recognition technique, a computer vision technique, a technique using a neural network, a heuristic technique, and/or the like, to automatically identify the position of the nerve tissue, the position of particular nerve bundles, the position of particular nerve branches, the position of particular nerves, and/or the like. This may allow the control device to display the nerve map in a manner that illustrates the positions of the nerve tissue at various levels of granularity, to display the nerve map relative to other objects and/or parts of the patient (e.g., relative to the prostate, relative to other tissues around the nerve tissue, relative to other body parts, relative to one or more devices that are part of the surgical device, and/or the like), and/or the like.

In this way, the surgical device obtains and provides the control device with the imaging data to allow the control device to display the imaging data in a manner that will assist with the prostatectomy.

Figure 1F:
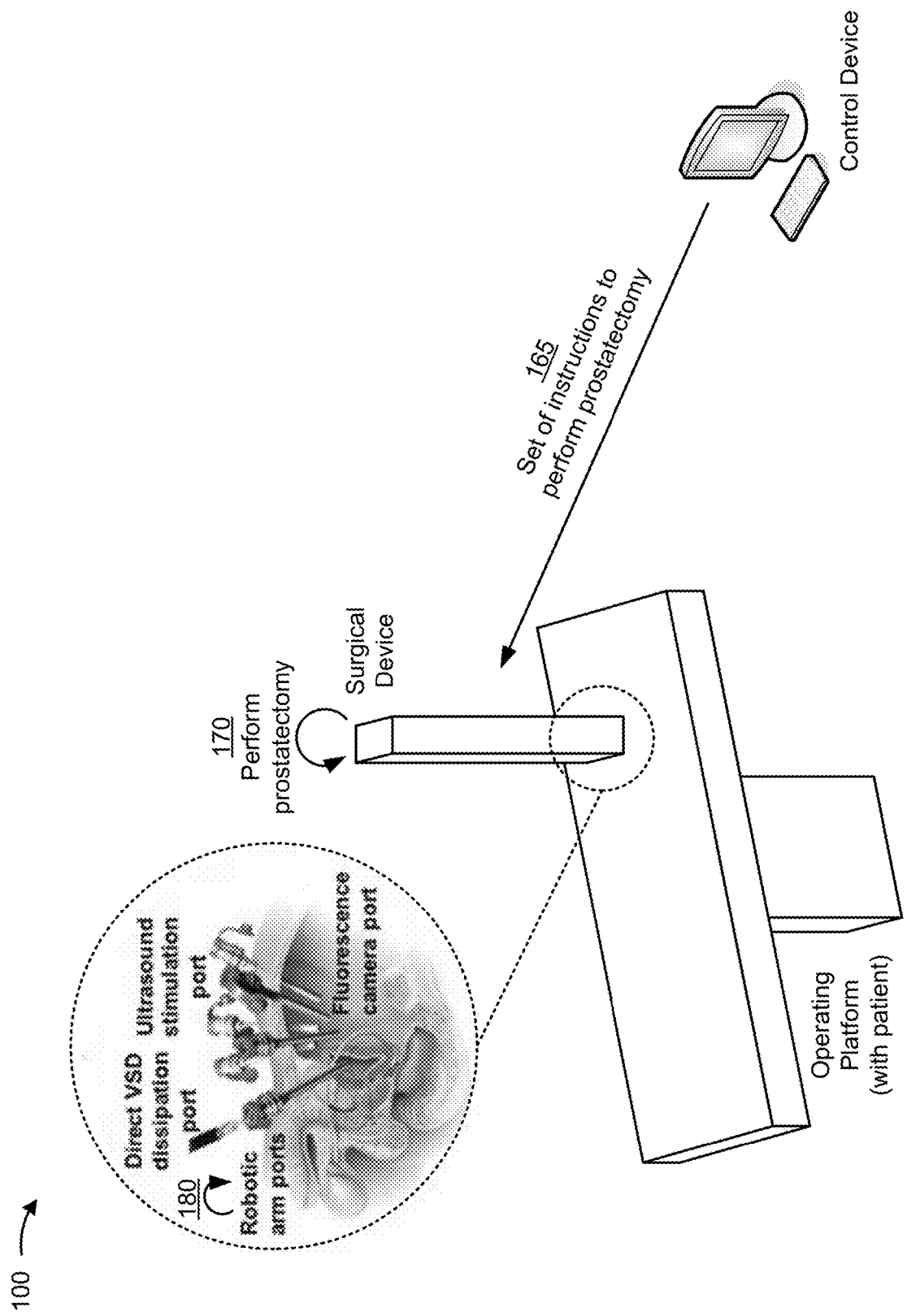

As shown in FIG. 1F, and by reference number 165, the control device may provide, to the surgical device, a set of instructions to perform the prostatectomy. For example, the control device may provide the surgical device with a set of instructions to perform the prostatectomy based on providing the imaging data for display, based on identifying the nerve map in the imaging data, based on a request from the surgeon, and/or based on another type of trigger. In this case, the control device may perform the prostatectomy to remove the prostatic fascia. For example, the control device may remove the prostatic fascia without damaging the nerve tissue based on the imaging data identifying positions of the nerve tissue at various levels of granularity (e.g., relative to the prostatic fascia, relative to other tissues near the nerve tissue, relative to one or more devices that are part of the surgical device, and/or the like).

In some implementations, the surgeon may perform the prostatectomy separate from the surgical device. For example, based on the imaging data being provided for display, the surgeon may view the imaging data and may perform the prostatectomy. In this way, the control device reduces a likelihood of negative surgical-related complications relative to other techniques that do not provide accurate nerve tissue imaging.

In some implementations, the control device may cause the surgical device to monitor an area associated with the prostate and/or the nerve tissue. For example, the control device may provide, to the surgical device, a set of instructions to monitor the area associated with the prostate and/or the nerve tissue. This may cause the surgical device to monitor the area by obtaining additional imaging data of fluorescent images and/or photoacoustic images (e.g., over a threshold time period after the prostatectomy is performed). Additionally, the surgical device may provide, to the control device, the additional imaging data of the fluorescent images and/or the photoacoustic images to the control device. If the control device determines that the fluorescence and/or the photoacoustic effect was present, it may be an indicator that the nerve tissue was stimulated and therefore was not damaged during the prostatectomy. Furthermore, the control device may provide the additional imaging data for display in a manner described elsewhere herein. In this way, the control device allows the surgical device to verify whether the prostatectomy was successful in a non-invasive manner (e.g., via a non-invasive stimulation through the spinal cord of the patient).

In some implementations, the control device may process the additional imaging data to identify functions of one or more nerves associated with the nerve tissue. For example, as the surgeon is performing the prostatectomy and/or after the surgery has been completed, the control device may periodically capture additional imaging data and may process the additional imaging data to identify functions of one or more nerves associated with the nerve tissue, states of one or more nerves associated with the nerve tissue, and/or the like. This may allow the additional imaging data to be displayed in real-time (or near real-time) such that the surgeon may view which nerves are more important than others (e.g., based on nerve functions), may view whether any of the nerves have been damaged during (and/or after) surgery (e.g., based on nerve status), and/or the like.

In this way, the control device and/or the surgical device improve surgical imaging by improving imaging resolution, imaging accuracy, imaging depth, and/or the like. For example, the control device and/or the surgical device improves surgical imaging by providing real-time or near real-time imaging of nerve tissue based on activating a VSD and utilizing ultrasound neuromodulation. Moreover, based on activating the VSD and utilizing ultrasound neuromodulation, the control device and/or the surgical device reduces a risk of surgical complications, a time to perform a surgery, an invasiveness of the surgery, and/or the like relative to other imaging techniques.

As indicated above, FIGS. 1A-1F are provided merely as one or more examples. Other examples are possible and may differ from what is described with regard to FIGS. 1A-1F. For example, there may be additional devices, fewer devices, different devices, or differently arranged devices than those shown in FIGS. 1A-1F. Furthermore, two or more devices shown in FIGS. 1A-1F may be implemented within a single device, or a single device shown in FIGS. 1A-1F may be implemented as multiple, distributed devices. Additionally, or alternatively, a set of devices (e.g., one or more devices) of example implementation(s) 100 may perform one or more functions described as being performed by another set of devices of example implementation(s) 100.

Figure 2:
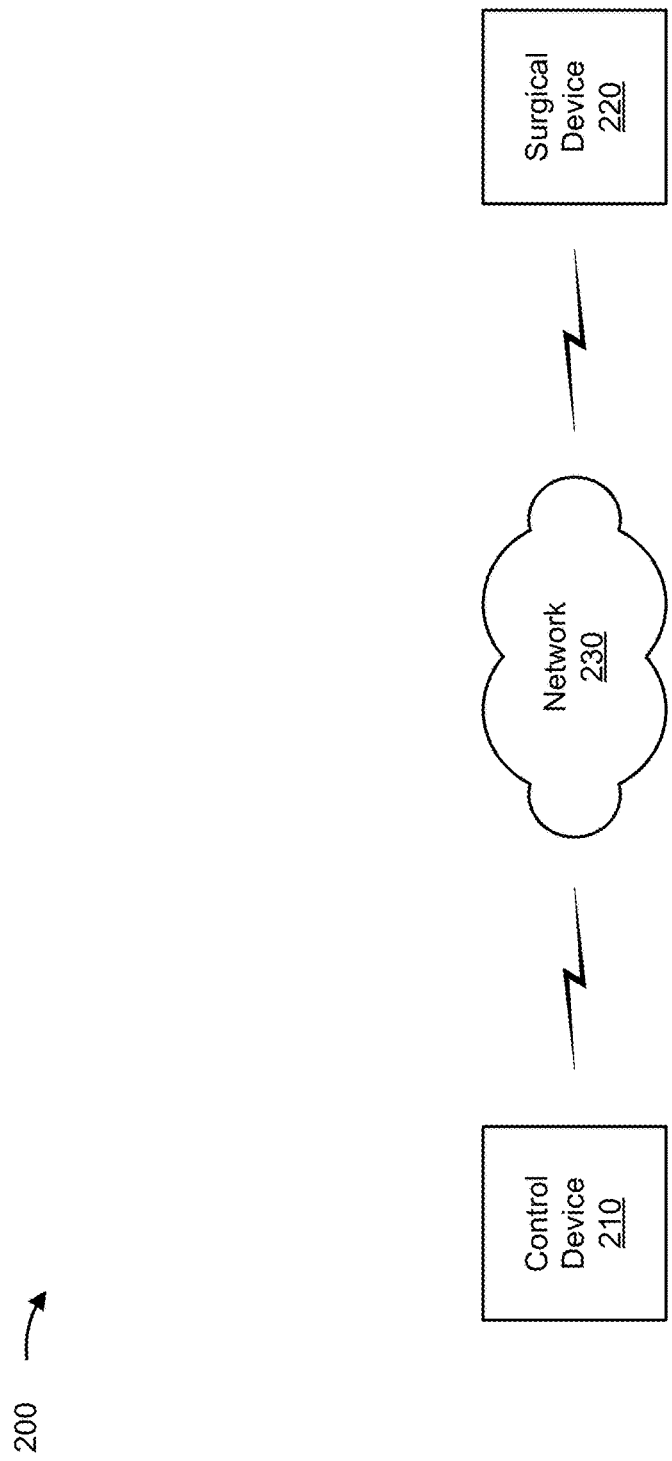
FIG. 2 is a diagram of an example environment in which systems and/or methods described herein may be implemented.

FIG. 2 is a diagram of an example environment 200 in which systems and/or methods, described herein, may be implemented. As shown in FIG. 2, environment 200 may include a control device 210, a surgical device 220, and a network 230. Devices of environment 200 may interconnect via wired connections, wireless connections, or a combination of wired and wireless connections.

Control device 210 includes one or more devices capable of receiving, generating, storing, processing, and/or providing information associated with controlling surgical device 220 and/or providing imaging of tissue. For example, control device 210 may include a communication and/or computing device, such as a computer (e.g., a laptop computer, a tablet computer, a handheld computer, a desktop computer), a mobile phone (e.g., a smart phone), a wearable device (e.g., a smart wristwatch, a pair of smart eyeglasses, a heads-up display device, a virtual reality device, a visual augmentation device, etc.), or a similar type of device. In some implementations, control device 210 includes one or more devices to control surgical device 220, such as a control console, a tele-manipulator, an end-effector, a remote surgery console, and/or the like. In some implementations, control device 210 may include a display device for providing a visualization of imaging data, an image processing device for processing the imaging data to generate the visualization, and/or the like.

Surgical device 220 includes one or more devices capable of receiving, generating, storing, processing, and/or providing information associated with imaging and/or a surgical procedure. For example, surgical device 220 may include a surgical robot with a set of devices to perform image capture, surgical incision, voltage sensitive dye staining, ultrasound excitation, and/or the like. Although some implementations, described herein, are described in terms of an integrated surgical device to perform a procedure, some implementations described herein may be used to obtain imaging data from a dedicated imaging device based on one or more procedures to enable capturing of the imaging data (e.g., voltage sensitive dye staining using a spraying tool, voltage sensitive dye activation using an ultrasound emitter, image capture using a white light image capturing device, a fluorescent image capturing device, a voltage membrane variation measurement device, and/or the like).

Network 230 includes one or more wired and/or wireless networks. For example, network 230 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
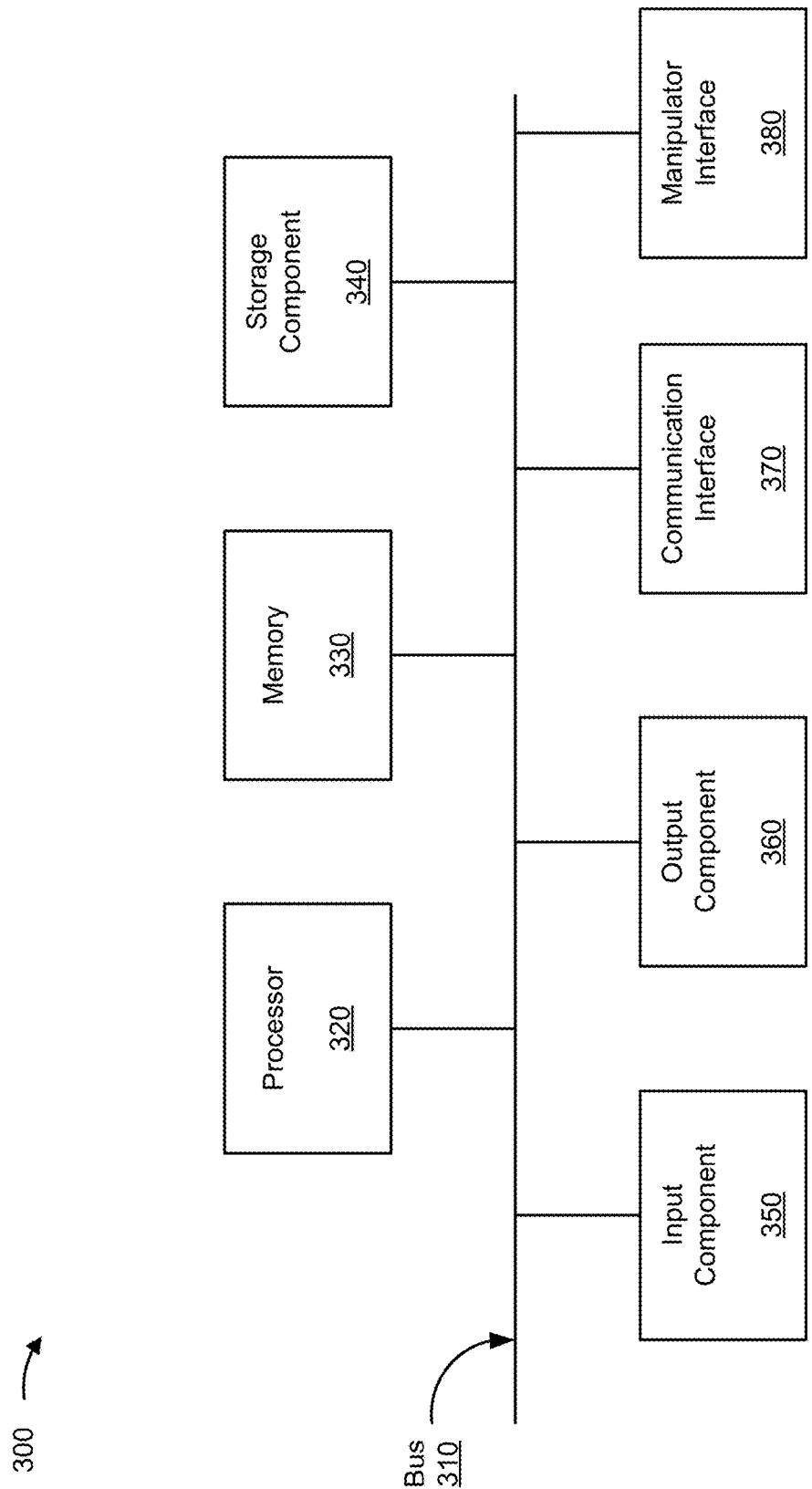
FIG. 3 is a diagram of example components of one or more devices of FIG. 2.

FIG. 3 is a diagram of example components of a device 300. Device 300 may correspond to control device 210 and/or surgical device 220. In some implementations, control device 210 and/or surgical device 220 may include one or more devices 300 and/or one or more components of device 300. As shown in FIG. 3, device 300 may include a bus 310, a processor 320, a memory 330, a storage component 340, an input component 350, an output component 360, a communication interface 370, and a manipulator interface 380.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Manipulator interface 380 includes a manipulator component to interact with a patient. For example, manipulator interface 380 may permit device 300 to control an end-effector, an image capture device, an ultrasound excitation device, a dye spraying device, a dye flushing device, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
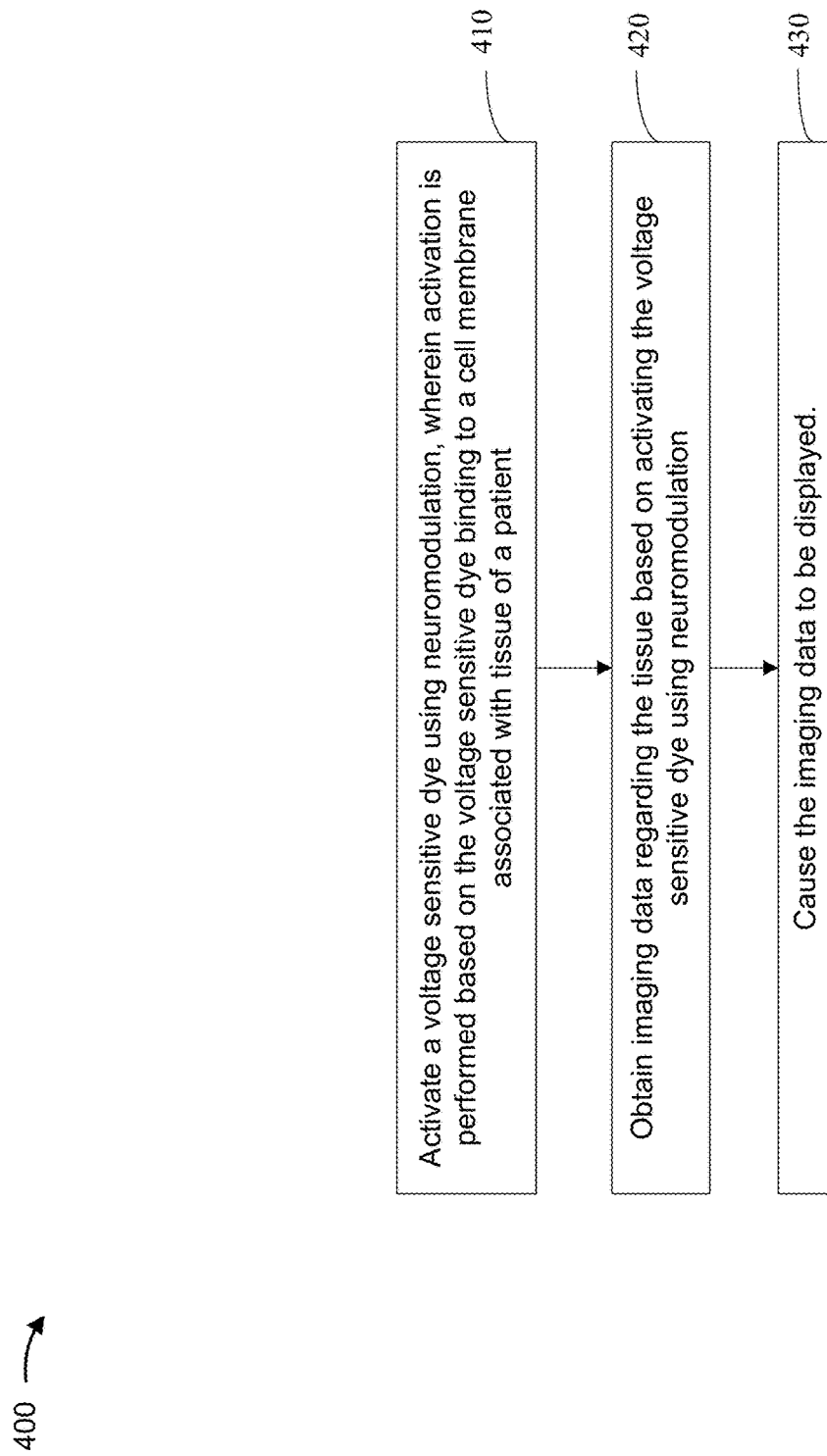
FIGS. 4-6 are flowcharts of one or more example processes for neuromodulation based nerve identification.

FIG. 4 is a flow chart of an example process 400 for neuromodulation based nerve identification. In some implementations, one or more process blocks of FIG. 4 may be performed by a surgical system that includes one or more devices (e.g., surgical device 220). In some implementations, one or more process blocks of FIG. 4 may be performed by another device or a group of devices separate from or including the surgical device, such as a control device (e.g., control device 210).

As shown in FIG. 4, process 400 may include activating a voltage sensitive dye using neuromodulation, wherein activation is performed based on the voltage sensitive dye binding to a cell membrane associated with tissue of a patient (block 410). For example, the surgical system (e.g., using processor 320, memory 330, storage component 340, input component 350, output component 360, communication interface 370, manipulator interface 380, and/or the like) may activate a voltage sensitive dye using neuromodulation, as described above. In some implementations, activation may be performed based on the voltage sensitive dye binding to a cell membrane associated with tissue of a patient.

As further shown in FIG. 4, process 400 may include obtaining imaging data regarding the tissue based on activating the voltage sensitive dye using ultrasound neuromodulation (block 420). For example, the surgical system (e.g., using processor 320, memory 330, storage component 340, input component 350, output component 360, communication interface 370, manipulator interface 380, and/or the like) may obtain imaging data regarding the tissue based on activating the voltage sensitive dye using ultrasound neuromodulation, as described above.

As further shown in FIG. 4, process 400 may include causing the imaging data to be displayed (block 430). For example, the surgical system (e.g., using processor 320, memory 330, storage component 340, input component 350, output component 360, communication interface 370, manipulator interface 380, and/or the like) may cause the imaging data to be displayed, as described above.

Process 400 may include additional implementations, such as any single implementation or any combination of implementations described below and/or in connection with one or more other processes described elsewhere herein.

In a first implementation, the surgical system may flush a first portion of the voltage sensitive dye. A second portion of the voltage sensitive dye that is bound to the tissue may not flushed. Additionally, when activating the voltage sensitive dye, the surgical system may activate the second portion of the voltage sensitive dye.

In a second implementation, alone or in combination with the first implementation, the surgical system may, when activating the voltage sensitive dye, activate the voltage sensitive dye in a manner that causes a voltage membrane variation to be identifiable by the imaging data.

In a third implementation, alone or in combination with one or more of the first and second implementations, the surgical system may, when obtaining the imaging data, obtain the imaging data using a camera that is capable of capturing fluorescent light and that is part of the surgical system.

In a fourth implementation, alone or in combination with one or more of the first through third implementations, when activating the voltage sensitive dye, the surgical system may activate the voltage sensitive dye using ultrasound neuromodulation to cause at least one of: a fluorescence, a photoacoustic effect.

In a fifth implementation, alone or in combination with one or more of the first through fourth implementations, the tissue may be nerve tissue associated with a prostate of a patient. In this case, when activating the voltage sensitive dye, the surgical system may use ultrasound neuromodulation to cause ultrasound energy to be directed toward a spinal cord of the patient to cause the voltage sensitive dye to be activated on the nerve tissue associated with the prostate of the patient.

In a sixth implementation, alone or in combination with one or more of the first through fifth implementations, wherein neuromodulation includes at least one of: ultrasound neuromodulation, neuromodulation using thermal energy, or neuromodulation using electrical current excitations.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
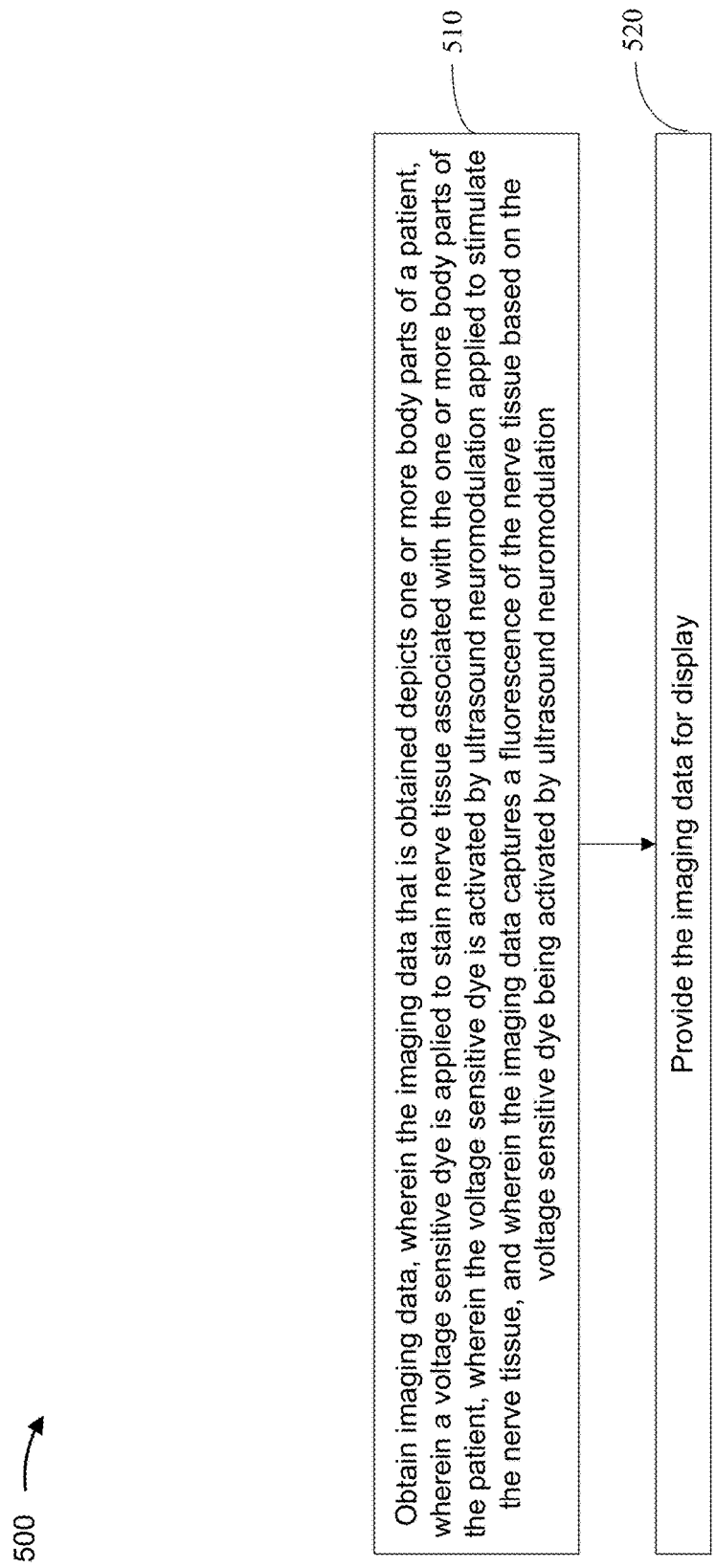

FIG. 5 is a flow chart of an example process 500 for neuromodulation based nerve identification. In some implementations, one or more process blocks of FIG. 5 may be performed by a device (e.g., control device 210). In some implementations, one or more process blocks of FIG. 5 may be performed by another device or a group of devices separate from or including the device, such as a surgical device (e.g., surgical device 220).

As shown in FIG. 5, process 500 may include obtaining imaging data, wherein the imaging data that is obtained depicts one or more body parts of a patient, wherein a voltage sensitive dye is applied to stain nerve tissue associated with the one or more body parts of the patient, wherein the voltage sensitive dye is activated by ultrasound neuromodulation applied to stimulate the nerve tissue, and wherein the imaging data captures a fluorescence of the nerve tissue based on the voltage sensitive dye being activated by ultrasound neuromodulation (block 510). For example, the control device (e.g., using processor 320, memory 330, storage component 340, input component 350, output component 360, communication interface 370, and/or the like) may obtain imaging data, as described above. In some implementations, the imaging data that is obtained may depict one or more body parts of a patient. In some implementations, a voltage sensitive dye may be applied to stain nerve tissue associated with the one or more body parts of the patient. In some implementations, the voltage sensitive dye may be activated by ultrasound neuromodulation applied to stimulate the nerve tissue. In some implementations, the imaging data may capture a fluorescence of the nerve tissue based on the voltage sensitive dye being activated by ultrasound neuromodulation.

As further shown in FIG. 5, process 500 may include providing the imaging data for display (block 520). For example, the control device (e.g., using processor 320, memory 330, storage component 340, output component 360, communication interface 370 and/or the like) may provide the imaging data for display, as described above.

Process 500 may include additional implementations, such as any single implementation or any combination of implementations described below and/or in connection with one or more other processes described elsewhere herein.

In a first implementation, the imaging data may be based on a photoacoustic effect caused by the voltage sensitive dye being activated by ultrasound neuromodulation.

In a second implementation, alone or in combination with the first implementation, the one or more body parts may include a prostate. In this case, the control device may communicate with a surgical system that includes one or more devices, to cause the surgical system to perform an incision to provide access to the prostate of the patient. Additionally, the control device may communicate with the surgical system to cause the surgical system to apply the voltage sensitive dye to stain the nerve tissue. Additionally, the control device may communicate with the surgical system to cause the surgical system to perform ultrasound neuromodulation to activate the voltage sensitive dye. Activation of the voltage sensitive dye may stimulate the nerve tissue. Additionally, when obtaining the imaging data, the control device may communicate with the surgical system to cause the surgical system to capture and provide the imaging data.

In a third implementation, alone or in combination with one or more of the first and second implementations, the one or more body parts may include a prostate. In this case, the control device may communicate with a surgical system that includes one or more devices to cause the surgical system to flush a first portion of the voltage sensitive dye. The first portion of the voltage sensitive dye may not bound to the nerve tissue. A second portion of the voltage sensitive dye may be bound to the nerve tissue and may be capable of excitation via performance of ultrasound neuromodulation.

In a fourth implementation, alone or in combination with one or more of the first through third implementations, the one or more body parts may include a prostate. In some implementations, the control device may provide, for display, information identifying a visible light image of the prostate. Additionally, the control device may overlay the visible light image of the prostate with the imaging data identifying the fluorescence of the nerve tissue that is associated with the prostate.

In a fifth implementation, alone or in combination with one or more of the first through fourth implementations, the control device may generate a visualization of the tissue based on the imaging data. Additionally, when providing the imaging data for display, the control device may provide the visualization of the tissue for display.

In a sixth implementation, alone or in combination with one or more of the first through fifth implementations, the control device may monitor the one or more body parts of the patient using a photoacoustic imaging technique. Additionally, the control device may cause additional imaging data, that is associated with the photoacoustic imaging technique, to be displayed.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
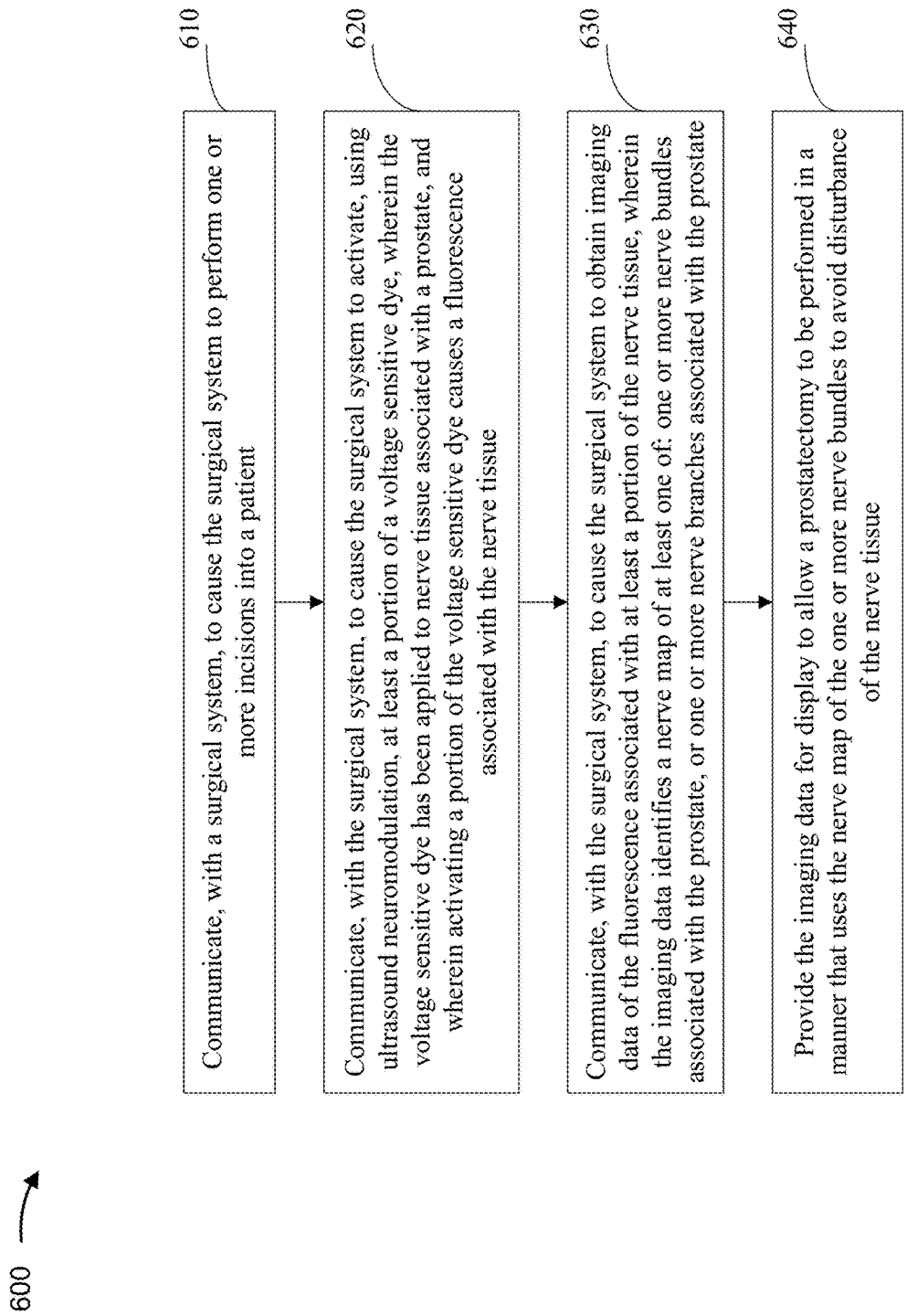

FIG. 6 is a flow chart of an example process 600 for neuromodulation based nerve identification. In some implementations, one or more process blocks of FIG. 6 may be performed by a device (e.g., control device 210). In some implementations, one or more process blocks of FIG. 6 may be performed by another device or a group of devices separate from or including the device, such as a surgical device (e.g., surgical device 220).

As shown in FIG. 6, process 600 may include communicating, with a surgical system, to cause the surgical system to perform one or more incisions into a patient (block 610). For example, the control device (e.g., using processor 320, memory 330, storage component 340, output component 360, communication interface 370, and/or the like) may communicate, with a surgical system, to cause the surgical system to perform one or more incisions into a patient, as described above.

As further shown in FIG. 6, process 600 may include communicating, with the surgical system, to cause the surgical system to activate, using ultrasound neuromodulation, at least a portion of a voltage sensitive dye, wherein the voltage sensitive dye has been applied to nerve tissue associated with a prostate, and wherein activating a portion of the voltage sensitive dye causes a fluorescence associated with at least a portion of the nerve tissue (block 620). For example, the control device (e.g., using processor 320, memory 330, storage component 340, output component 360, communication interface 370, and/or the like) may communicate, with the surgical system, to cause the surgical system to activate, using ultrasound neuromodulation, at least a portion of a voltage sensitive dye, as described above. In some implementations, the voltage sensitive dye may have been applied to nerve tissue associated with a prostate. In some implementations, activating a portion of the voltage sensitive dye may cause a fluorescence associated with at least a portion of the nerve tissue.

As further shown in FIG. 6, process 600 may include communicating, with the surgical system, to cause the surgical system to obtain imaging data of the fluorescence associated with at least the portion of the nerve tissue, wherein the imaging data identifies a nerve map of at least one of: one or more nerve bundles associated with the prostate, or one or more nerve branches associated with the prostate (block 630). For example, the control device (e.g., using processor 320, memory 330, storage component 340, input component 350, output component 360, communication interface 370, and/or the like) may communicate, with the surgical system, to cause the surgical system to obtain imaging data of the fluorescence associated with at least the portion of the nerve tissue, as described above. In some implementations, the imaging data may identify a nerve map of at least one of: one or more nerve bundles associated with the prostate, or one or more nerve branches associated with the prostate.

As further shown in FIG. 6, process 600 may include providing the imaging data for display, to allow a prostatectomy to be performed in a manner that uses the nerve map to avoid disturbance of the one or more nerve bundles (block 640). For example, the control device (e.g., using processor 320, memory 330, storage component 340, output component 360, communication interface 370, and/or the like) may provide the imaging data for display, to allow a prostatectomy to be performed in a manner that uses the nerve map to avoid disturbance of the one or more nerve bundles, as described above.

Process 600 may include additional implementations, such as any single implementation or any combination of implementations described below and/or in connection with one or more other processes described elsewhere herein.

In a first implementation, the portion of the voltage sensitive dye may be a first portion. Additionally, the control device may communicate, with the surgical system, to cause the surgical system to stain a surface of the prostate of the patient using the voltage sensitive dye. The staining may be performed for a threshold period of time. Additionally, the control device may communicate, with the surgical system, to cause the surgical system to flush a second portion of the voltage sensitive dye from the patient after expiration of the threshold period of time. The first portion of the voltage sensitive dye may remain bound at a cell membrane level to the one or more nerve bundles associated with the prostate.

In a second implementation, alone or in combination with the first implementation, the control device may, when communicating with the surgical system to cause the surgical system to activate the voltage, provide a set of instructions to the surgical system to cause the surgical system to activate the voltage sensitive dye, using ultrasound neuromodulation, in a manner that causes a photoacoustic effect.

In a third implementation, alone or in combination with one or more of the first and second implementations, the control device may, when communicating with the surgical system to cause the surgical system to obtain the imaging data of the fluorescence associated with the one or more nerve bundles, provide a set of instructions to the surgical system to cause the surgical system to obtain the imaging data.

In a fourth implementation, alone or in combination with one or more of the first through third implementations, the control device may, when communicating with the surgical system to cause the surgical system to activate at least the portion of the voltage sensitive dye, apply ultrasound energy using at least one of: non-invasive stimulation through a spinal cord of the patient, laparoscopic stimulation at a surgical site of the patient, or transrectal stimulation via a rectum of the patient.

In a fifth implementation, alone or in combination with one or more of the first through fourth implementations, the control device may communicate, with the surgical system, to cause the surgical system to monitor one or more body parts of the patient using a photoacoustic imaging technique. Additionally, the control device may receive, from the surgical system, additional imaging data, that is associated with the photoacoustic imaging technique. Additionally, the control device may provide the additional imaging data for display.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

The foregoing disclosure provides illustration and description but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Some implementations are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, or the like.

Certain user interfaces have been described herein and/or shown in the figures. A user interface may include a graphical user interface, a non-graphical user interface, a text-based user interface, and/or the like. A user interface may provide information for display. In some implementations, a user may interact with the information, such as by providing input via an input component of a device that provides the user interface for display. In some implementations, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   activating, by a surgical system that includes one or more devices, a voltage sensitive dye using neuromodulation,
   wherein the voltage sensitive dye is activated based on the voltage sensitive dye binding to a cell membrane associated with a tissue of a patient, and
   wherein activating the voltage sensitive dye causes a fluorescence and a photoacoustic effect;
   obtaining, by the surgical system, imaging data regarding the tissue based on the fluorescence and the photoacoustic effect,
   wherein the imaging data includes fluorescence images that depict the fluorescence and photoacoustic images that are based on the photoacoustic effect caused by activating the voltage sensitive dye, and
   wherein the imaging data identifies a nerve map of at least one of:
      one or more nerve bundles associated with the tissue of the patient, or
      one or more nerve branches associated with the tissue of the patient;
   causing, by the surgical system, the nerve map to be displayed,
   wherein the displayed nerve map depicts different nerves using different colors based on one or more of a confidence level associated with a respective identified location of a nerve or a level of importance of a function of the nerve;
   obtaining, by the surgical system and based on the voltage sensitive dye being activated using the neuromodulation, additional imaging data regarding the tissue over a threshold period of time after a performance of a surgical operation; and
   determining, based on the additional imaging data, whether the tissue of the patient was damaged during the surgical operation.

2. The method of claim 1, further comprising:
   flushing, by the surgical system, a first portion of the voltage sensitive dye,
   wherein a second portion of the voltage sensitive dye that is bound to the cell membrane associated with the tissue is not flushed; and
   wherein activating the voltage sensitive dye comprises:
      activating the second portion of the voltage sensitive dye.

3. The method of claim 1, wherein activating the voltage sensitive dye comprises:
   activating the voltage sensitive dye in a manner that causes a voltage membrane variation to be identifiable by the imaging data.

4. The method of claim 1, wherein obtaining the imaging data comprises:
   obtaining the imaging data using a camera that is capable of capturing fluorescent light and that is part of the surgical system,
   wherein the imaging data identifies the fluorescence associated with the voltage sensitive dye being activated using the neuromodulation.

5. The method of claim 1, wherein activating the voltage sensitive dye comprises:
   activating the voltage sensitive dye using the neuromodulation to cause the fluorescence;
   emitting a pulse laser light at nerve tissue associated with the fluorescence to cause thermal elastic expansion of the tissue;
   capturing sound waves caused by the thermal elastic expansion of the tissue;
   converting the sound waves into electrical signals; and
   converting the electrical signals into data corresponding to the photoacoustic images.

6. The method of claim 1, wherein the tissue is nerve tissue associated with a prostate of the patient; and
   wherein activating the voltage sensitive dye comprises:
      activating the voltage sensitive dye using ultrasound neuromodulation by causing ultrasound energy to be directed toward a spinal cord of the patient to cause the voltage sensitive dye to be activated on the nerve tissue associated with the prostate of the patient.

7. The method of claim 1, wherein the neuromodulation includes at least one of:
   ultrasound neuromodulation,
   neuromodulation using thermal energy, or
   neuromodulation using electrical current excitations.

8. A device, comprising:
   one or more memories; and
   one or more processors, communicatively coupled to the one or more memories, to:
      obtain imaging data,
         wherein the imaging data that is obtained depicts one or more body parts of a patient,
         wherein a voltage sensitive dye is applied to stain nerve tissue associated with the one or more body parts of the patient,
         wherein the voltage sensitive dye is activated,
         wherein a first portion of the imaging data includes fluorescence images capturing a fluorescence of the nerve tissue based on the voltage sensitive dye being activated, and
         wherein a second portion of the imaging data includes photoacoustic images that are based on a photoacoustic effect caused by activating the voltage sensitive dye;
      provide the imaging data for display,
         wherein the displayed imaging data depicts different nerves using different colors based on one or more of a confidence level associated with a respective identified location of a nerve or a level of importance of a function of the nerve;
      obtain, after performance of a surgical operation and over a threshold period of time, additional imaging data that depicts the one or more body parts of the patient,
         wherein the additional imaging data includes additional fluorescence images capturing the fluorescence of the nerve tissue based on the voltage sensitive dye being activated by the ultrasound neuromodulation and additional photoacoustic images that are based on the photoacoustic effect caused by activating the voltage sensitive dye; and determine, based on the additional imaging data, whether the nerve tissue was damaged during the surgical operation.

9. The device of claim 8, wherein the voltage sensitive dye is activated by ultrasound neuromodulation.

10. The device of claim 8, wherein the one or more body parts include a prostate of the patient; and
wherein the one or more processors are further to:
communicate with a surgical system that includes one or more devices, to cause the surgical system to perform an incision to provide access to the prostate of the patient;
communicate with the surgical system to cause the surgical system to apply the voltage sensitive dye to stain the nerve tissue; and
communicate with the surgical system to cause the surgical system to activate the voltage sensitive dye, wherein activating the voltage sensitive dye stimulates the nerve tissue; and
wherein the one or more processors, when obtaining the imaging data, are to:
communicate with the surgical system to cause the surgical system to capture and provide the imaging data.

11. The device of claim 8, wherein the one or more body parts include a prostate of the patient; and wherein the one or more processors are further to:
communicate with a surgical system that includes one or more devices to cause the surgical system to flush a first portion of the voltage sensitive dye,
wherein the first portion of the voltage sensitive dye is not bound to the nerve tissue, and
wherein a second portion of the voltage sensitive dye is bound to the nerve tissue and is capable of excitation via a performance of ultrasound neuromodulation.

12. The device of claim 8, wherein the one or more body parts include a prostate of the patient; and wherein the one or more processors are further to:
provide, for display, information identifying a visible light image of the prostate of the patient; and
overlay the visible light image of the prostate of the patient with the first portion of the imaging data.

13. The device of claim 8, wherein the one or more processors are further to:
generate a visualization of the nerve tissue based on the fluorescence images and the photoacoustic images; and
wherein the one or more processors, when providing the imaging data for display, are to:
provide the visualization of the nerve tissue for display.

14. The device of claim 8, wherein the one or more processors are further to:
monitor the one or more body parts of the patient using the imaging data.

15. A method, comprising:
communicating, by a device and with a surgical system, to cause the surgical system to perform one or more incisions into a patient;
communicating, by the device and with the surgical system, to cause the surgical system to activate, using ultrasound neuromodulation, at least a portion of a voltage sensitive dye,
wherein the voltage sensitive dye has been applied to nerve tissue associated with a prostate of the patient, and
wherein activating the at least the portion of the voltage sensitive dye causes a fluorescence associated with at least a portion of the nerve tissue and a photoacoustic effect;
communicating, by the device and with the surgical system, to cause the surgical system to obtain imaging data,
wherein the imaging data includes fluorescence imaging data of the fluorescence associated with the at least the portion of the nerve tissue and photoacoustic imaging data based on the photoacoustic effect caused by activating the voltage sensitive dye, and
wherein the imaging data identifies a nerve map of at least one of:
one or more nerve bundles associated with the prostate of the patient, or
one or more nerve branches associated with the prostate of the patient;
providing, by the device, the nerve map for display, to allow a prostatectomy to be performed in a manner that uses the nerve map to avoid disturbance of the nerve tissue,
wherein the displayed nerve map depicts different nerves using different colors based on one or more of:
a confidence level associated with a respective identified location of a nerve, or
a level of importance of a function of the nerve;
communicating, by the device and with the surgical system, to cause the surgical system to obtain additional imaging data of the fluorescence associated with the at least the portion of the nerve tissue,
wherein the additional imaging data is obtained over a threshold period of time after a performance of the prostatectomy; and
determining, based on the additional imaging data, whether the disturbance of the nerve tissue was avoided during the performance of the prostatectomy.

16. The method of claim 15, wherein the at least the portion of the voltage sensitive dye is a first portion;
wherein the method further comprises:
communicating, by the device and with the surgical system, to cause the surgical system to stain a surface of the prostate of the patient using the voltage sensitive dye,
wherein the staining is performed for a period of time; and
communicating, by the device and with the surgical system, to cause the surgical system to flush a second portion of the voltage sensitive dye from the patient after an expiration of the period of time,
wherein the first portion of the voltage sensitive dye remains bound at a cell membrane level to the nerve tissue associated with the prostate of the patient.

17. The method of claim 15, wherein communicating with the surgical system to cause the surgical system to activate the voltage sensitive dye comprises:
providing a set of instructions to the surgical system to cause the surgical system to activate the voltage sensitive dye, using the ultrasound neuromodulation, in a manner that causes the photoacoustic effect.

18. The method of claim 15, wherein communicating with the surgical system to cause the surgical system to obtain the imaging data of the fluorescence associated with the nerve tissue comprises:
  providing a set of instructions to the surgical system to cause the surgical system to obtain the imaging data,
    wherein the nerve map, that is identified by the imaging data, depicts the nerve tissue in a manner that allows a function and a status of one of the different nerves, that are part of the nerve tissue, to be identified.

19. The method of claim 15, wherein communicating with the surgical system to cause the surgical system to activate the at least the portion of the voltage sensitive dye comprises:
  applying ultrasound energy using at least one of:
    non-invasive stimulation through a spinal cord of the patient,
    laparoscopic stimulation at a surgical site of the patient, or
    transrectal stimulation via a rectum of the patient.

20. The method of claim 15, further comprising:
  communicating, by the device and with the surgical system, to cause the surgical system to monitor one or more body parts of the patient using the imaging data.

* * * * *